United States Patent [19]
Dowsett et al.

[11] Patent Number: 6,080,986
[45] Date of Patent: Jun. 27, 2000

[54] SECONDARY ION MASS SPECTROMETER WITH APERTURE MASK

[75] Inventors: Mark Graeme Dowsett, West Midlands, United Kingdom; Johann L. Maul, Indersdorf, Germany

[73] Assignee: Atomika Instruments GmbH, Oberschleibheim, Germany

[21] Appl. No.: 09/094,380

[22] Filed: Jun. 9, 1998

[30] Foreign Application Priority Data

Jun. 9, 1997 [DE] Germany .......................... 197 24 265

[51] Int. Cl.[7] ..................................................... H01J 49/26
[52] U.S. Cl. ........................... 250/309; 250/307; 250/306
[58] Field of Search ................................... 250/309, 281, 250/282, 306, 307

[56] References Cited

U.S. PATENT DOCUMENTS

| | | | |
|---|---|---|---|
| 4,611,120 | 9/1986 | Bancroft et al. | 250/309 |
| 4,748,325 | 5/1988 | Slodzian . | |
| 4,992,661 | 2/1991 | Tamura et al. | 250/309 |
| 5,350,919 | 9/1994 | Hirano et al. . | |

FOREIGN PATENT DOCUMENTS

| | | |
|---|---|---|
| 4205752 | 8/1993 | Germany . |
| 59-180361 | 12/1984 | Japan . |
| 60-39750 | 3/1985 | Japan . |
| 61-58941 | 12/1986 | Japan . |
| 62-160650 | 7/1987 | Japan . |

OTHER PUBLICATIONS

Manfred Grasserbauer; Secondary Ion Mass Spectrometry; (1994); ol. 28; p. 222–232.

H. Bolouri and J S Colligan; A simple efficient SIMS apparatus for use on accelerator beam lines; (1982); vol. 32; p. 293–295.

Helmut Liebl; Optimum Sample Utilization In Secondary Ion Mass Spectrometry; (1981); p. 183–188; North–Holand Publishing Co.

Helmut Liebl; Combined Electrostatic Objective And Emission Lenses For Microcharacterization Of Surfaces; (1983); p. 511–514; Elsevier Scientific Publishing Company, Amsterdam.

*Primary Examiner*—Kiet T. Nguyen
*Attorney, Agent, or Firm*—Helfgott & Karas, P.C.

[57] ABSTRACT

In a secondary ion mass spectrometer an aperture mask (3), which is not part of the secondary ion optics (5) of the spectrometer, is arranged very near to the surface of a specimen (1) to be analyzed, for example a semiconductor. The primary and secondary ions pass through the aperture (3A) in the aperture mask (3). The position of the specimen relative to the aperture mask dictates the location on the specimen (1) to be analyzed. The outer dimension of the mask is larger than the field of view of the secondary ion optics (5). Due to the masked region the fringe areas of the specimen are shielded ionoptically so that they cannot result in any falsification of the electric field. An electrical dc or ac potential can be applied to the mask (3) so that the electric field between the aperture (3A) and the specimen (1) can be additionally influenced. A contact device (3B) can be applied between the mask (3) and the specimen (1) for preventing electrical charging of the specimen (1).

11 Claims, 2 Drawing Sheets

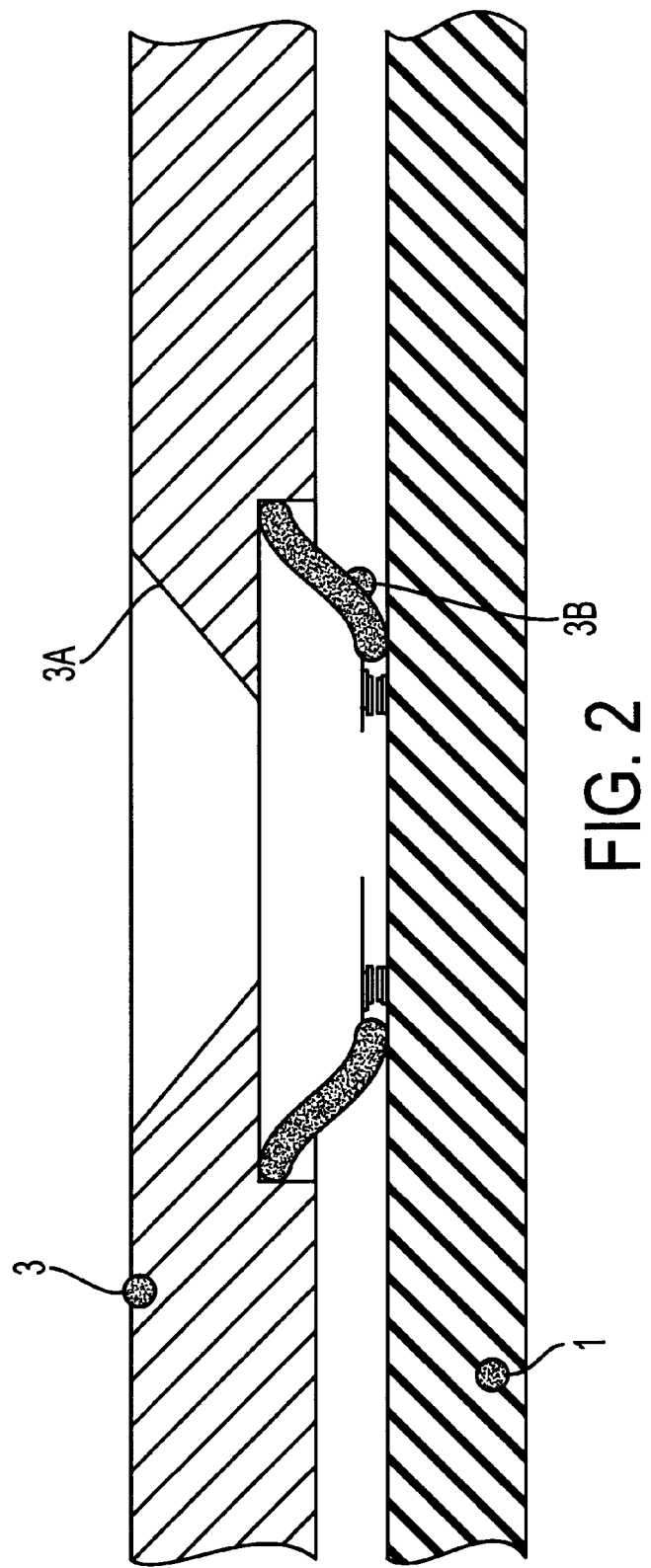

SECONDARY ION MASS SPECTROMETER WITH APERTURE MASK

The invention relates to a secondary ion mass spectrometer as set forth in the preamble of claim 1 and a secondary ion mass spectrometry method as set forth in the preamble of claim 5.

The salient field of application of secondary ion mass spectrometers is surface and in-depth analysis of doped semiconductors in microelectronics. Setting a predetermined concentration profile of a specific dopant in the depth of a semiconductor specimen is of decisive significance for proper functioning of a device to be fabricated from the semiconductor material. This is why a very high accuracy and reproducibility in sensing a doping profile (down to 1% and lower) is demanded also for the analysis of the solid-state body. Identical doping profiles at differing locations of the specimen must also result in identical signal characteristics in analysis.

The principle of analysis in secondary ion mass spectrometry and the arrangement involved often necessitate, however, different locations of the specimen to be subjected to different potential conditions. More particularly, the fringe areas of a semiconductor specimen differ usually from the areas located further inwards due to direction and intensity of the electric field of the extraction optics for the secondary ions changing at the fringe. The transmittance of the secondary ion optics may also be disturbed by movement of the specimen stage should irregularities in the specimen stage or fringe thereof come into the field of view of the secondary ion optics in the course of analysis. The electric field in the total region between the secondary ion optics and the specimen dictates, however, the transmission of secondary ions from the specimen up to the entrance aperture of the extraction optics. By consequence, analysis done especially at the center of the specimen and at the fringe of a homogeneously doped semiconductor furnishes different results although the doping profiles to be analyzed are identical at both locations.

It is thus an object of the present invention to define a secondary ion mass spectrometer with which a specimen can be analyzed irrespective of the geometric circumstances of the location being analyzed. This object is achieved by the characterizing features of the claims 1 and 5. Advantageous embodiments are defined in the sub-claims.

In the secondary ion mass spectrometer in accordance with the invention an aperture mask is arranged very near to but separated from the specimen to be analyzed, the primary and secondary ions passing through the aperture. The location on the specimen to be analyzed is attained by laterally shifting the solid-state specimen under the positionally located or fixed mask, i.e. the secondary ion optics "see" the specimen or the location to be analyzed on the specimen through the aperture in the mask. The outer dimension of the mask is larger than the field of view of the secondary ion optics. The distance between the specimen and the mask is very small, i.e. of the order of 2 mm or less. Therefore the aperture mask might also be called virtual sample mask. The mask thus shields off the effects of the fringe area of the solid-state specimen ionoptically so that these cannot result in any falsification of the electric field. Accordingly, in shifting the specimen the potential conditions and thus the secondary ion transmission too, remain constant, as a result of which there is no longer any difference in the results of analysis, irrespective of whether the location to be analyzed is at the fringe of the specimen or roughly in the middle of the specimen.

In the following embodiments of the present invention are illustrated with respect to the attached drawings, in which FIG. 1A shows a section view of a first embodiment of the secondary ion mass spectrometer according to the present invention;

FIG. 2 shows an enlarged section view of a mask arrangement according to a second embodiment of the secondary ion mass spectrometer of the present invention.

Figure 1A:
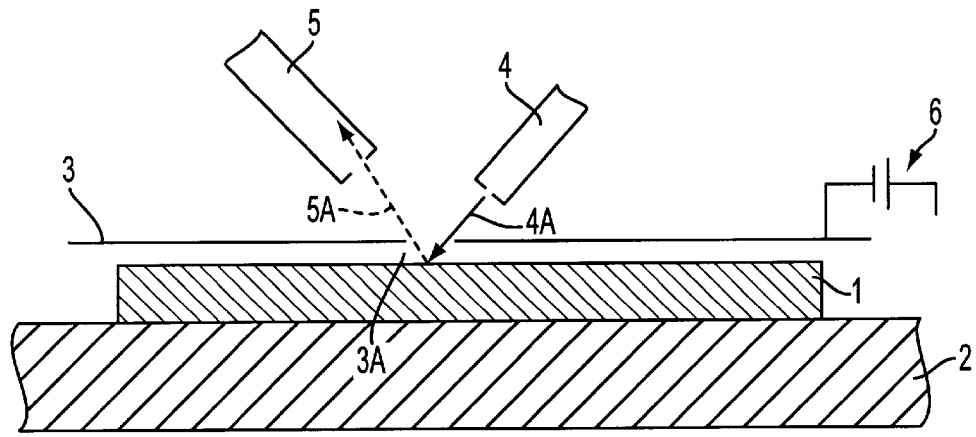
FIG. 1B shows a plan view of the spectrometer arrangement of FIG. 1A.

In FIG. 1A a section view of a first embodiment of the present invention is illustrated schematically (not true to scale).

A specimen 1 of a solid-state body, for example a semiconductor, to be analyzed is located on a specimen stage 2 and is held in place thereby. A beam of primary ions 4A from a primary ion source 4 is focussed on the surface of the specimen. Tho beam of secondary ions 5A emitted by the specimen is "seen" by the secondary ion optics 5, indicated schematically, and is analyzed in a mass spectrometer and a detector connected thereto.

Located above the specimen is the aperture mask 3 having the aperture 3A for the passage of the primary and secondary ion beam. This aperture is preferably circular and has a diameter in the range of a few millimeters to a few centimeters. The outer dimension of the mask 3 is larger than the field of view of the secondary ion optics, i.e. changes in the distribution of the electric field in time and space as may be caused, for instance, by fringe areas of the specimen or of the specimen stage or by changes in the geometry of the specimen stage relative to the secondary ion optics have no effect on the electric fields of the secondary ion optics due to the shielding afforded by the mask, and thus are not sensed in analysis. The field of view of the secondary ion optics relative to the specimen is restricted by the arrangement in accordance with the invention to the region of the aperture 3A.

The mask or in particular the mask aperture is positioned spaced away from the specimen by very little, preferably by less than 2 mm, more preferably by less than one millimeter. The mask is therefore almost a part of the sample and may thus be called virtual sample mask.

By means of a voltage source 6 the mask can be subjected to an electric potential. This can be of advantage for transmittance of the secondary ion optics and thus for the quality of in-depth profile analysis, for instance. The electric potential of the mask may be identical to the specimen potential or it may differ therefrom. For the application of modulation techniques a time-related potential may also be applied to the mask.

By laterally shifting the specimen 1 beneath the mask 3 a desired specimen location is selected. By setting a predetermined voltage at the mask 3 either a particularly high secondary ion transmission and/or a particularly low fringe effect can be achieved.

Figure 1B:
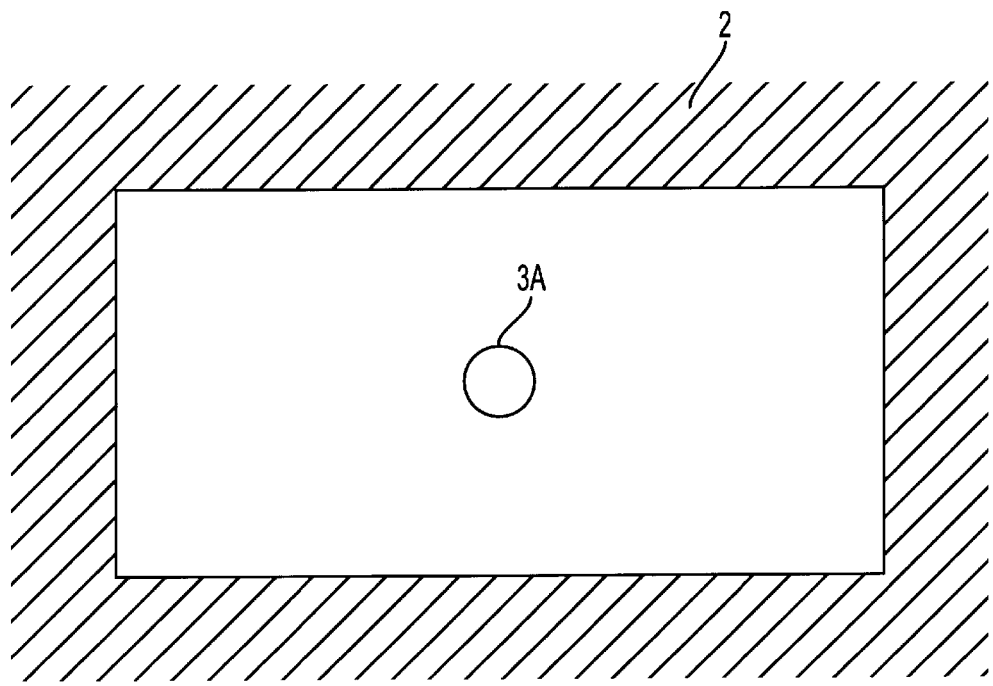

In FIG. 1B a plan view of the arrangement shown in FIG. 1A is illustrated. The solid-state specimen 1 is shifted laterally relative to the aperture mask 2 fixed in position three-dimensionally for selecting a location to be analyzed. The specimen 1 may be adjustable perpendicular to the aperture mask 3 to ensure a constant spacing of the aperture from the specimen surface.

The aperture mask 3 is illustrated in FIG. 1A as a flat plate. However, the aperture mask 3 may have in theory any other desired shape as long as the restriction of the field of view of the secondary ion optics essential to the invention is achieved in the region of the aperture 3A with shielding of the remaining region of the field of view.

In FIG. 2 an enlarged section view of a mask arrangement according to a second embodiment of the present invention is shown.

The aperture 3A of the mask has preferably circular cross section. It can be seen that in an upper portion of the mask 3 the diameter of tho aperture 3A gradually decreases from the upper surface of the mask 3 towards the wafer 1 to be analyzed. In a lower portion of the mask 3 the aperture 3A comprises a recessed portion for receiving a ring-shaped contact device 3B. The contact device 3B is electrically conductive and thus provides for continuous electrical contact between the mask 3 and the wafer 1. The contact device 3B is preferably made of a soft material. It is tightly secured in the recessed portion of the mask 3 and is contacting the specimen surface at the front surface.

The contact device 3B provides for a continuous balance in the electrical potential between the mask 3 and the wafer 1. The electrical charging of the wafer 1 can thus be prevented.

Of course the contact device 3B may have a form different from that as shown in FIG. 2.

What is claimed is:

1. A secondary ion mass spectrometer for analyzing a specimen (1) including a primary ion source (4) for the emission and focussing of a beam of primary ions on a desired location on the surface of the specimen (1), secondary ion optics (5) for the extraction of secondary ions emitted by the specimen (1), a mass spectrometer and a detector for secondary ions, comprising:

a mask (3), which is not part of the secondary ion optics (5), having an aperture (3A) for passage of the primary ions and secondary ions and arranged very near to the surface of the specimen (1) to be analyzed in such a way, so that the mask (3) and the specimen (1) may be shifted laterally with respect to each other, and wherein the outer dimension of the mask (3) being larger than the field of view of the secondary ion optics (5).

2. A secondary ion mass spectrometer as set forth in claim 1, wherein the distance between the mask (3) and the specimen (1) is less than 2 mm.

3. A secondary ion mass spectrometer as set forth in claim 1, further comprising a dc or ac voltage source (6) for applying an electric potential to the mask (3).

4. A secondary ion mass spectrometer as set forth in claim 1, further comprising a contact device (3b) for electrically contacting the mask (3) and the specimen (1).

5. A secondary ion mass spectrometer as set forth in claim 1, wherein the distance between the mask (3) and the specimen (1) is less than 1 mm.

6. A method for analyzing a specimen (1) using secondary ion mass spectrometry, comprising the steps of:

providing a secondary ion mass spectrometer, said secondary ion mass spectrometer comprising:

a primary ion source (4) for the emission and focussing of a beam of primary ions on a desired location on the surface of the specimen (1), secondary ion optics (5) for the extraction of secondary ions emitted by the specimen (1), a mass spectrometer, a detector for secondary ions, and a mask (3), which is not part of the secondary ion optics (5), having an aperture (3A) for passage of the primary ions and secondary ions and arranged very near to the surface of the specimen (1) to be analyzed in such a way, so that the mask (3) and the specimen (1) may be shifted laterally with respect to each other, and wherein the outer dimension of the mask (3) is larger than the field of view of the secondary ion optics (5), selecting a location to be analyzed on the specimen (1) by laterally shifting the specimen (1) and the mask (3) with respect to each other without changing the ion-optical conditions as related to the specimen (1), emitting primary ions (4A) by the primary ion source (4) and focussing the primary ions (4A) on the selected location, and extracting secondary ions emitted by the solid-state specimen through secondary ion optics and analyzing them in the mass spectrometer.

7. A method as set forth in claim 6, wherein the distance between the mask (3) and the specimen (1) is kept at a constant value of less than 2 mm.

8. A method as set forth in claim 7, wherein the mask is subjected to an electrical dc or ac potential.

9. A method as set forth in claim 6, wherein the mask is subjected to an electrical dc or ac potential.

10. A method as set forth in claim 6, wherein the distance between the mask (3) and the specimen (1) is kept at a constant value of less than 1 mm.

11. A method as set forth in claim 10, wherein the mask is subjected to an electrical dc or ac potential.

* * * * *